US012584868B2

(12) United States Patent
Mulloth

(10) Patent No.: US 12,584,868 B2
(45) Date of Patent: Mar. 24, 2026

(54) METHOD FOR SCANNING OF AN OBJECT IN A SCANNING APPARATUS

(71) Applicant: ROLLS-ROYCE plc, London (GB)

(72) Inventor: Akhil Mulloth, Derby (GB)

(73) Assignee: ROLLS-ROYCE PLC, London (GB)

( * ) Notice: Subject to any disclaimer, the term of this patent is extended or adjusted under 35 U.S.C. 154(b) by 152 days.

(21) Appl. No.: 18/536,868

(22) Filed: Dec. 12, 2023

(65) Prior Publication Data

US 2024/0219321 A1 Jul. 4, 2024

(30) Foreign Application Priority Data

Jan. 4, 2023 (GB) ..................................... 2300064

(51) Int. Cl.
| | |
|---|---|
| *G01N 23/046* | (2018.01) |
| *A61B 6/00* | (2024.01) |
| *A61B 6/02* | (2006.01) |
| *A61B 6/03* | (2006.01) |

(52) U.S. Cl.
CPC ........... *G01N 23/046* (2013.01); *A61B 6/027* (2013.01); *A61B 6/035* (2013.01); *A61B 6/542* (2013.01); *G01N 2223/419* (2013.01)

(58) Field of Classification Search
CPC ........... G01N 23/046; G01N 2223/419; G01N 2223/63; A61B 6/027; A61B 6/035; A61B 6/542
See application file for complete search history.

(56) References Cited

U.S. PATENT DOCUMENTS

| | | | |
|---|---|---|---|
| 4,601,050 A | 7/1986 | Tanaka | |
| 4,803,639 A | 2/1989 | Steele et al. | |
| 5,023,895 A | 6/1991 | McCroskey et al. | |

(Continued)

FOREIGN PATENT DOCUMENTS

| | | |
|---|---|---|
| CN | 101435784 A | 5/2009 |
| EP | 1 672 357 A2 | 6/2006 |

(Continued)

OTHER PUBLICATIONS

Jun. 19, 2023 Search Report issued in British Patent Application No. 2300064.9.

(Continued)

*Primary Examiner* — Courtney D Thomas
(74) *Attorney, Agent, or Firm* — Oliff PLC

(57) ABSTRACT

There is provided a method for scanning of an object in a scanning apparatus. The method comprises placing the object into a jacket which surrounds the object or a part of the object to be scanned. The volume of the jacket surrounding the object is solid or filled with a filling material. The jacket is disposed on a support of the scanning apparatus, so that the jacket is positioned between an imaging beam emitting element and an imaging beam receiving element oppositely disposed to either side of the support. The support is rotatable relative to the emitting and receiving elements about an axis of rotation to allow creation of an image from projections each taken at a different relative angle of rotation. The method further comprises operating the scanning apparatus at the multiple relative angles of rotation to produce an image of the object.

20 Claims, 15 Drawing Sheets

(56) References Cited

U.S. PATENT DOCUMENTS

| | | | | |
|---|---|---|---|---|
| 5,119,408 | A | * | 6/1992 | Little .................... G01N 23/046 |
| | | | | 378/10 |
| 5,237,598 | A | | 8/1993 | Albert |
| 5,420,788 | A | | 5/1995 | Vissers |
| 6,041,132 | A | * | 3/2000 | Isaacs .................... G06T 11/008 |
| | | | | 600/407 |
| 6,094,269 | A | | 7/2000 | Ben-Dove et al. |
| 2006/0056577 | A1 | | 3/2006 | Hunt et al. |
| 2010/0183115 | A1 | | 7/2010 | Van Stevendaal et al. |
| 2012/0321033 | A1 | | 12/2012 | Stearns et al. |
| 2014/0119497 | A1 | * | 5/2014 | Guzman .............. G01N 33/241 |
| | | | | 250/255 |
| 2015/0355113 | A1 | | 12/2015 | Christoph et al. |
| 2016/0030133 | A1 | | 2/2016 | Ramsey et al. |
| 2016/0334344 | A1 | | 11/2016 | Freeman et al. |
| 2016/0334345 | A1 | | 11/2016 | Freeman et al. |
| 2017/0039735 | A1 | | 2/2017 | Can et al. |
| 2021/0270756 | A1 | | 9/2021 | Ursella |
| 2022/0042930 | A1 | | 2/2022 | Stiebeiner et al. |
| 2022/0178851 | A1 | | 6/2022 | Yun et al. |
| 2023/0010730 | A1 | | 1/2023 | Schlecht et al. |
| 2024/0044812 | A1 | | 2/2024 | Rothschild |
| 2024/0295509 | A1 | | 9/2024 | Mulloth |

FOREIGN PATENT DOCUMENTS

| | | | |
|---|---|---|---|
| EP | 3 093 652 | A1 | 11/2016 |
| EP | 3 764 090 | A1 | 1/2021 |
| GB | 1005557 | A | 9/1965 |
| GB | 2605606 | A | 10/2022 |
| WO | 2019/077950 | A1 | 4/2019 |
| WO | 2019/192860 | A1 | 10/2019 |
| WO | 2022/087357 | A1 | 4/2022 |

OTHER PUBLICATIONS

Jun. 26, 2023 Search Report issued in British Patent Application No. 2300062.3.

Jun. 26, 2023 Search Report issued in British Patent Application No. 2300063.1.

U.S. Appl. No. 18/536,834, filed Dec. 12, 2023 in the name of Akhil Mulloth.

U.S. Appl. No. 18/536,847, filed Dec. 12, 2023 in the name of Akhil Mulloth.

May 31, 2024 Extended European Search Report Issued in European Patent Application No. 23214302.4.

May 28, 2024 Extended European Search Report Issued in European Patent Application No. 23214301.6.

May 28, 2024 Extended European Search Report Issued in European Patent Application No. 23214303.2.

* cited by examiner

50

| S10 |
| :---: |

| S20 |
| :---: |

| S30 |
| :---: |

METHOD FOR SCANNING OF AN OBJECT IN A SCANNING APPARATUS

TECHNICAL FIELD

The present disclosure relates to a method for scanning of objects in a scanning apparatus such as a computed tomography, CT, scanning apparatus. The present disclosure relates further to a combination of a scanning apparatus for scanning of an object and an object in the scanning apparatus.

BACKGROUND

The present disclosure is relevant to many scanning technologies, but a primary application is three-dimensional x-ray computed tomography, or CT, which combines multiple x-ray images to recreate a 3-dimensional, 3D, volume, so may be referred to as 3DCT scanning. An x-ray source produces polychromatic x-rays that penetrate a part and form an x-ray image on a detector. The object is (usually) rotated through 360 degrees while being imaged multiple times. The x-ray images are combined via a process called reconstruction to produce a 3D representation of the object. Surface determination is then performed to separate the object volume from the background. Subsequently, cross sections of the object may be viewed by the user. Various alternative apparatuses for CT scanning are seen in known arrangements. In a medical scanner, for example, the object is fixed with the source and detector orbiting the object. There are other options on the market that allow the height to change to take a helical scan or do a slight shift to the height to do a pixel shift scan.

CT and other scanning may be used to inspect non-line-of-sight areas of parts, for example vanes and turbine blades, that are not accessible to alternative inspection techniques such as bore scopes. This is important to be able to deliver novel geometries, for example for cast metal turbine blades and additively manufactured components.

The known arrangements teach that 3DCT scans of cast metal turbine blades, for example, are to be performed on one part at a time as the composition of the part may effectively attenuate the CT scanning x-ray beam. The known arrangements also teach that the object is to be positioned in the middle of the scanning frame, for instance with a vertical axis of rotation of a rotatable CT scanning platform extending through the object. The object may be inclined to create an angle between the axis of rotation and a longitudinal axis of the object. In this case, the orientation of the object may be selected to minimise the path length that the x-ray penetrates. Known arrangements teach that bigger and thicker objects generally produce lower quality scans as they create more beam scattering. Aiming to reduce beam hardening and poor penetration, the known arrangements teach to increase the voltage of the x-ray emitting apparatus and to use a physical or software-based scatter correction. It is desirable to improve the quality and/or efficiency of CT scanning of objects. Increasing the voltage produces a higher number of x-rays capable of penetrating more material. The same part scanned at a higher voltage will produce a higher quality image for numerous reasons. However, as taught in known arrangements, the voltage should be limited as too high a voltage will reduce the difference in contrast between two materials as the material will attenuate fewer x-rays.

A cylinder is the ideal shape to scan because it has the same thickness whatever the angle of rotation of the table with respect to the emitter and receiver. Components with complex cross sections and/or cross sections that change along their length such as turbine blades and vanes face particular scanning challenges. A turbine blade may present an aerofoil cross-section with a leading edge and a trailing edge face. The leading-edge cross-section is thicker than the trailing edge cross-section. The aerofoil section of the object may have a concave blade surface on one side bounded at either end by the leading and trailing edges and a convex blade surface on the other side. Optimising the CT scan parameters for all of the parts at the same time is difficult. In particular, the concave surface of the blade has the potential to concentrate or converge scattered x-rays and create a high level of noise on the concave side, leading to concave side (or concave wall) effects. A concave wall effect produces image artifacts formed on or around the image of the object due to beam hardening and haloing.

SUMMARY

According to one aspect, there is provided a method for scanning of an object in a scanning apparatus. The method comprises placing an object into a jacket which surrounds the object or a part of the object to be scanned. A volume of the jacket surrounding the object is solid (a solid jacket volume) or filled with a filling material. The jacket is disposed on a support of the scanning apparatus so that the jacket is positioned between an imaging beam emitting element and an imaging beam receiving element oppositely disposed to either side of the support. The support is rotatable relative to the emitting and receiving elements about an axis of rotation to allow creation of an image from projections each taken at a different relative angle of rotation. The method further comprises operating the scanning apparatus at the multiple relative angles of rotation to produce an image of the object.

Of course, if the jacket surrounds a part of the object to be scanned, the remaining part of the object not to be scanned may be disposed on the support so that the jacket and part of the object to be scanned are in the scanning region.

Surprisingly, the inventor has found that use of a surrounding jacket (which is thus in a fixed stationary relationship with the part) and with a solid jacket volume or filling material within the jacket can significantly improve the scan quality for many objects, especially those with complex cross sections and/or cross sections that change along their length.

In one scenario, the scanning apparatus is a two-dimensional or three-dimensional computational tomography, CT, scanning apparatus with a table or platform which is rotatable about a vertical axis, and with oppositely disposed x-ray emitter and receiver units to either side of the table. The jacket or vessel or container may be directly supported on the platform or held within a jig (or on a support in the form of a jig). It may extend at an angle to the vertical to facilitate cross-sections at preferred angles through the jacket and object.

The method may further comprise filling the volume surrounding the object within the jacket with the filling material. The filling material may be poured or added into the jacket after the object has been placed into the jacket.

The filling material or solid jacket volume may have an imaging beam attenuation close to the imaging beam attenuation of the material of the object (such as within 20% or 10% of the imaging beam attenuation of the material of the object). The filling material or solid jacket volume may have substantially the same imaging beam attenuation as the imaging beam attenuation of the material of the object. The effectively constant attenuation coefficient across the filling material or solid jacket volume and object may improve the image quality for each projection taken at varying angles. Averaging out the material thickness by, for example filling in any concave surfaces, may also reduce artifacts caused by x-rays scattering off the object's surface and the concave wall effect, even with a filling material or solid jacket volume having a different level of attenuation from the object.

The filling material may be in the form of pieces, powder, grains or fluid. The filling material may, for example, be either metal powder or polymer powder and thus may be poured into the jacket. This allows the filling material to completely surround the object or the part of the object to be scanned, completely filling any voids or gaps between the object and the jacket. This may provide an approximately constant material thickness (path length) for each projection, thereby improving image quality of the scan.

The object may be formed of a metal: pure, alloy or composite, for example. In this case, the powder may be in the form of metal powder of the same material as the object or the solid jacket volume may be of the same metal as the object. As before, matching the (mass) attenuation coefficient of the powder or solid with the object, by using the same material as the object, may improve image quality. In the case where the object is a cast turbine blade or other object with a concave surface, the metal powder or solid may fill the concavity, thereby reducing image artifacts caused by scattering and beam hardening, for example.

The jacket may have a circular cross-section or substantially circular cross-section. It may comprise one or more walls together forming a spherical or part spherical surface or may have a cylindrical side wall extending from a base. The jacket may completely surround the object or may surround the part of the object to be scanned. If the jacket is hollow (to receive a filling material) and has a spherical or part spherical surface, it may be constructed in pieces to allow a cap (forming part of the spherical or part spherical surface) to be added to a main part (also forming part of the spherical or part spherical surface) once the jacket has been filled. If there is a base and cylindrical side wall, the base and side wall may be formed of a polymer film or wall and may contain the filling material.

The jacket may have a solid volume or may contain the filling material, and in either case may surround the object so that the thickness of material to be penetrated is approximately constant for all projections. Thus, the image quality and contrast of the scan may be improved. The polymer film or wall may have a relatively low imaging beam attenuation as compared to, for instance, the metal powder. Hence, the polymer may have a minimal effect on the image quality of the scan. The jacket, containing the object, may be disposed on the support or, of course, if the jacket surrounds the part of the object to be scanned, the part of the object not contained within the jacket may be disposed on the support.

There may be a border region surrounding or partially surrounding the object in the jacket with an imaging beam attenuation different from the imaging beam attenuation of the object. For example, the border region has a lower imaging beam attenuation than the imaging beam attenuation of the object. The region may be formed of a material with a lower density than the object, for example the region may be an air gap.

The object may be wrapped or coated in one or more films, sleeves or walls, for example a polymer film such as cling film or a polymer membrane or a polymer bag or a polymer wall (which may be 3D printed), to provide a boundary between the object and the filling material or the solid jacket volume. The one or more films, sleeves or walls may form the border region. The object may be wrapped in the film, inserted into the sleeve or placed between moulded walls before placing it in the jacket. This may prevent the object contacting the filling material or solid volume and may therefore prevent contamination of the object. Any suitable material may be used to cover the object before it is placed in the jacket. The film, wall or sleeve may have a low imaging beam attenuation and may therefore aid identification of the object in the jacket by providing a contrast in the scan image at the object's surface and act as or delimit the border region mentioned above.

The jacket may be offset from the axis of rotation so that its centre (for example centre of mass and/or centre of symmetry) is displaced from the axis, for example by at least half the minimum extent of the jacket taken in any horizontal plane. The jacket may be positioned so that no part of the jacket or no part to be scanned of the object intersects the axis of rotation.

Any scannable object and any shape of scannable object may be used in the method. For example, the object may be made of metal or composite as mentioned above, or polymer or a mixture of materials. The object can be cast or moulded or machined or 3D printed (additive manufacturing), for example. The object may be a simple shape, such as a cylinder or sphere, or a more complex object such as a component for use in a machine. Hence the object may be a blade or vane or other complex manufactured part. The object may be a turbine blade. The blade may have a leading edge and a trailing edge separated by blade surfaces. In this case the blade can have any orientation with respect to the axis of rotation. However, the inventor has surprisingly found that a better image quality results when the orientation of the turbine blade within the jacket positions the leading edge closer to the axis of rotation than the trailing edge (that is, a line drawn from the axis to the extremity of the leading edge is shorter than the corresponding line drawn to the extremity of the trailing edge).

Additionally, or alternatively, for a shape of turbine blade having a leading edge and a trailing edge separated by a concave blade surface opposite to a convex blade surface, the jacket may be disposed on the support so that the convex blade surface is closer to the axis of rotation than the concave blade surface. Indeed, this arrangement is not limited to turbine blades, any object may have a concave surface opposite a convex surface and be correspondingly positioned. This orientation too, can provide better image quality, for example because the concave surface is facing away from the axis, which has been seen to reduce the concave wall effect. By positioning the blade with the concave side facing away from the axis, poor image contrast may be improved as the concave side may be in a brighter region of the scan. However, in some scenarios, due to complicated internals, or the leading edge having overly curved and thick geometries, the concave side may be pointed towards the axis of rotation and still be in the bright region to produce a good quality scan. The combination of the filling material or solid jacket volume occupying the volume surrounding the object in the jacket and the concave blade surface facing away from the axis has proved particularly advantageous.

Of course, the turbine blade is not limited to a convex surface and concave surface. For example, the turbine blade may have a substantially flat blade surface opposite a concave surface or two concave surfaces opposite one another or any other combination of surfaces from known arrangements.

A plurality of objects may be placed in a jacket and/or a plurality of jackets may be disposed on the support. In examples, no part to be scanned, that is no part of interest from the scan, or no part of any of the objects (or jackets) intersect the axis of rotation. The objects may be substantially similar or identical, such as a particular size of turbine blade or may be different from each other. Each object may have its centre (for example centre of mass or symmetry) displaced from the axis, for example by at least half the minimum extent of the object taken in any horizontal plane. The plurality of objects and/or plurality of jackets may be disposed so that no part to be scanned or no part of any of the objects or jackets or filling material or solid jacket volume intersects the axis of rotation.

The plurality of jackets may be disposed on the support so that a notional line drawn from the emitting element to the receiving element through the axis of rotation intersects two or more of the plurality of jackets for at least a third or over half of the projections. That is, the projections, which are taken at equally spaced angular positions around the axis of rotation, may cover 360 degrees of rotation, and the projections over at least 120 degrees (or 180 degrees) may then intersect one or more jackets. With this density of jacket spacing, and therefore object positioning comes an increase in efficiency and, contrary to the established view, the inventor has found that any decline in quality is not significant. In fact, the inventor has come to the surprising realisation that the scan quality may be improved as a larger amount of material allows for more power to be used for the scan without oversaturating the detector. Also, scanning parameters such as the power to voxel size ratio, sometimes referred to as the power to voxel ratio, are easier to adjust to desirable values when the thickness to be scanned of the objects varies less. So, positioning of the jackets in which the rays pass through at least one jacket for more of the projections reduces a variation in thickness to be scanned and can make parameter setting easier. Optimising the software scanning parameters may further improve the scanning efficiency.

As before, the plurality of objects placed within the jacket(s) may be turbine blades each with a leading edge and a trailing edge separated by a concave blade surface opposite to a convex blade surface. The orientation of (a) turbine blade(s) within each jacket may position the convex blade surface of each blade to face the axis of rotation, with the advantages enumerated above.

The plurality of jackets may be positioned in any suitable arrangement. For example, they may form a pattern on vertices of a notional regular geometric figure centred on the axis of rotation. Taking the arrangement in which the turbine blade is placed in the jacket, for example, a jacket may be positioned on all the three vertices (corners) of a triangle, the four vertices of a square, or the five vertices of a pentagon, or the six vertices of a hexagon etc.: any notional figure can be used. A further plurality of jackets or objects may be positioned in a pattern on the vertices of a further notional regular geometric figure centred on the axis of rotation and inside the notional regular geometric figure. An object or objects of the further plurality of objects may have substantially similar geometries to the plurality of objects or may be different from the plurality of objects and/or each other. Additionally or alternatively to the further plurality of jackets or objects, an attenuating object or objects such as a solid cylinder may be disposed in the inner region, for example centred on the axis.

The objects in the jackets may be oriented to provide rotational symmetry of the pattern of objects (and jackets) about the axis of rotation. Optionally, the objects may be substantially similar or identical in construction and disposed on the support in the jackets so that the order of rotational symmetry is equal to the number of vertices of the notional regular geometric figure. Of course, the objects and/or the jackets may be constructed of different materials but have substantially similar forms and therefore still exhibit rotational symmetry. Alternatively, the objects may have different shapes and still possess a rotational symmetry about the axis of rotation in terms of positioning. Further, the jackets may have different shapes but may be orientated so that objects within them exhibit rotational symmetry. Of course, any combination of jacket and object shape discussed above may possess rotational symmetry.

The jackets may be positioned on some but not all of the vertices of the notional regular geometric figure (for example two of the four vertices of a square). In this case, all of the jackets may be positioned to one side of a plane along which the axis of rotation extends (as seen in plan view for a vertical axis and horizontal support all the parts are to one side of a straight line drawn through the axis of rotation). Surprisingly, the inventor has found that such an asymmetrical arrangement, with half of the available space left empty, provides a better quality. By orientating the jackets so that the leading edge of a turbine blade, for example on one vertex of a square, is adjacent to the trailing edge of a second turbine blade on the next vertex, even better image quality of the second turbine blade may be obtained.

In another arrangement, there is a plurality of objects in a jacket at a vertex of the notional figure. In this arrangement, the objects may be grouped in a configuration, for example directly adjacent to each other and/or centred on the vertex. For example, jackets with four objects in them may be positioned at each vertex of a square (seen in plan view with a vertical axis of rotation).

The objects may be elongate (such as the turbine blades previously described) and a shape of the configuration formed by the combined shape of the objects in the configuration may have a lower aspect ratio than a single one of the objects. This can give a shape of the configuration which is more similar to the "ideal" cylindrical shape for scanning in which thickness of material to be penetrated is constant for all the projections. In other words, the configuration can minimise the variation in material thickness between the emitter and receiver penetrated at the multiple relative angles of rotation. The aspect ratio of the configuration is less than two thirds, or even less than half, of the aspect ratio of a single one of the objects. The aspect ratio of the combined shape may be computed using the aspect ratio of a rectangular bounding box around the two (or more) cross sections. Evening out the material path length using this configuration may further improve the scan quality when combined with the improvement from the filling material or solid jacket volume.

When the objects are turbine blades, the blades may be positioned in the configuration in alternate head-to-toe configuration with the leading edge of one blade positioned adjacent to the trailing edge of the adjacent blade within the jacket. The chords of all (or both) the blades (for example, all two, three, four or more blades) in the configuration may be aligned. If the blade has convex and concave blade surfaces, and there is a jacket, with two blades positioned within it, at each vertex, the concave surface of one turbine blade at a vertex may face the concave surface of the other turbine blade. Alternatively, the convex surface of one turbine blade may be opposite the convex surface of an adjacent turbine blade.

In a further aspect, there is provided a combination of a scanning apparatus for scanning of an object and a filled jacket in the scanning apparatus (all as previously described). The scanning apparatus comprises: a support for the object and an imaging beam emitting element and an imaging beam receiving element oppositely disposed to either side of the support. The support is rotatable relative to the emitting and receiving elements about an axis of rotation to allow creation of an image of the object from projections each taken at a different relative angle of rotation. The filled jacket comprises a jacket and an object (or part of an object if the jacket only surrounds a part of interest of the object), the jacket surrounding the object or the part of the object to be scanned. A volume of the jacket surrounding the object is solid or filled with a filling material, as described above. The filled jacket is positioned on the support; so that when the scanning apparatus is operated at the multiple relative angles of rotation it produces an image of the object within the jacket.

The apparatus for scanning the objects in the jackets may be a two-dimensional or three-dimensional computational tomography, CT, scanning apparatus, such as a three-dimensional, 3DCT, scanning apparatus. The imaging beam emitting element may emit an energy beam within the x-ray region of the electromagnetic spectrum. The emitted x-rays may form a polychromatic x-ray spectrum. The x-rays may be formed by a tungsten metal element within the imaging element. Of course, the emitting element may emit other energy forms such as gamma rays or ultrasound or any other energy beam suitable for scanning. The imaging beam emitting element and the imaging beam receiving element may be oppositely disposed to either side of the support.

The support may be a table which rotates about a vertical axis and the objects may be disposed on the support. Alternatively, the support may be fixed and the imaging beam emitting element and the imaging beam receiving element may rotate around a vertical axis centred on the support.

The skilled person will appreciate that except where mutually exclusive, a feature described in relation to any one of the above aspects may be applied mutatis mutandis to any other aspect. Furthermore, except where mutually exclusive, any feature described herein may be applied to any aspect and/or combined with any other feature described herein.

BRIEF DESCRIPTION OF THE DRAWINGS

Examples will now be described with reference to the accompanying drawings, which are purely schematic and not to scale, and in which.

DETAILED DESCRIPTION

Figure 1:
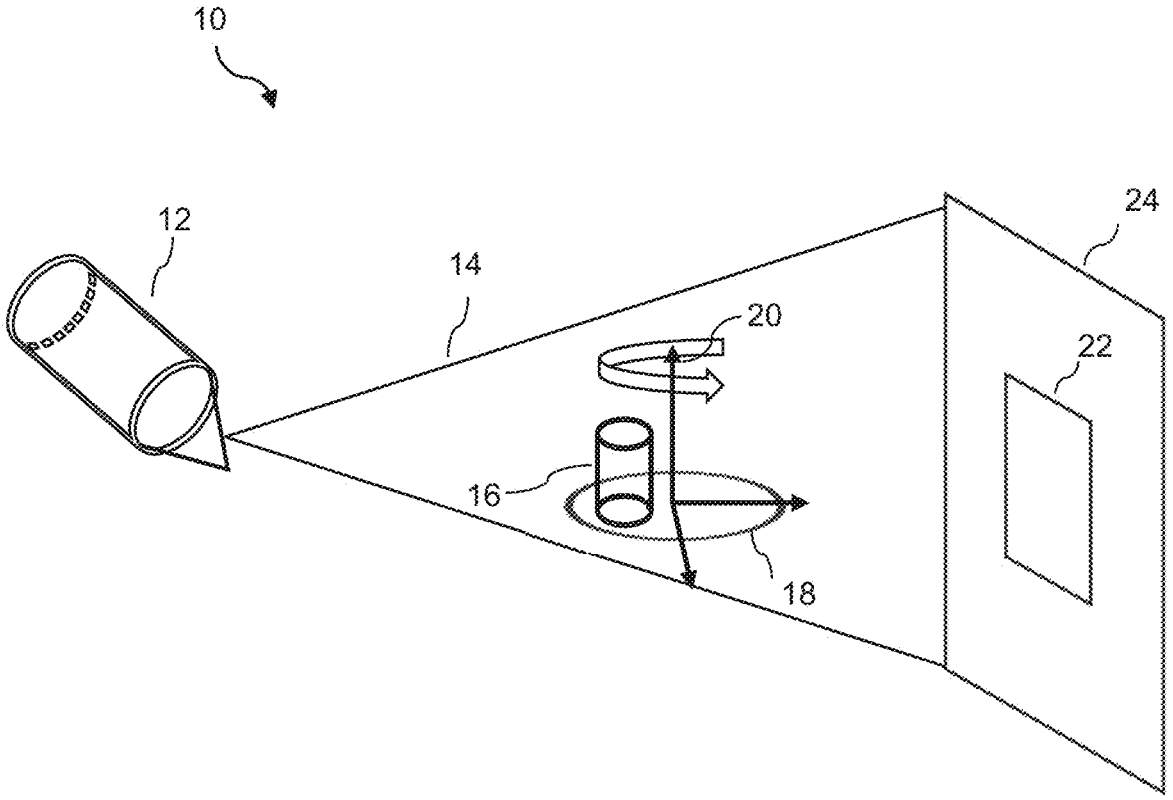
FIG. 1 is a schematic illustration showing an exemplary 3-dimensional CT scanning arrangement.

FIG. 1 illustrates the basic principles of an exemplary 3DCT scanning technique of a type which may be used in the method discussed herein. A 3D computer tomography (CT) scanning apparatus 10 may be used to perform a volumetric scan. The 3DCT scanning apparatus 10 comprises an imaging beam (i.e. x-ray), emitting element 12, a support 18 and an imaging beam (i.e. x-ray), detecting element 24. The volumetric scan may be any scan which is capable of generating a 3-dimensional (3D) image of an object 16 positioned on the support 18 and contained within an x-ray beam cone 14. The x-ray emitting element 12 generates the x-ray beam cone 14 which may comprise polychromatic x-rays (not shown). The support (usually a table on which the object or a jig is positioned) may be configured to rotate about a (usually vertical) axis of rotation 20 so that the object 16 positioned directly or indirectly on the support rotates about the axis of rotation. The object is shown here as a simple cylinder. The polychromatic x-rays penetrate the object and are received by the x-ray detecting element. A volumetric x-ray image 22 of the object is formed from the output of the x-ray detecting element. For example, the output may be processed in a manner known per se to form one or more two-dimensional images in the form of "slices" (cross-sections) through the object.

As will be appreciated, in order to capture complete slices through the relevant part of the object via the type of technique described above, the part of the object being scanned should remain entirely within the x-ray beam cone whilst it is rotated.

Figure 2:
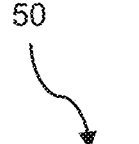
FIG. 2 is a flow chart showing steps of a method for scanning of an object or a plurality of objects in a scanning apparatus.
Figure 2:
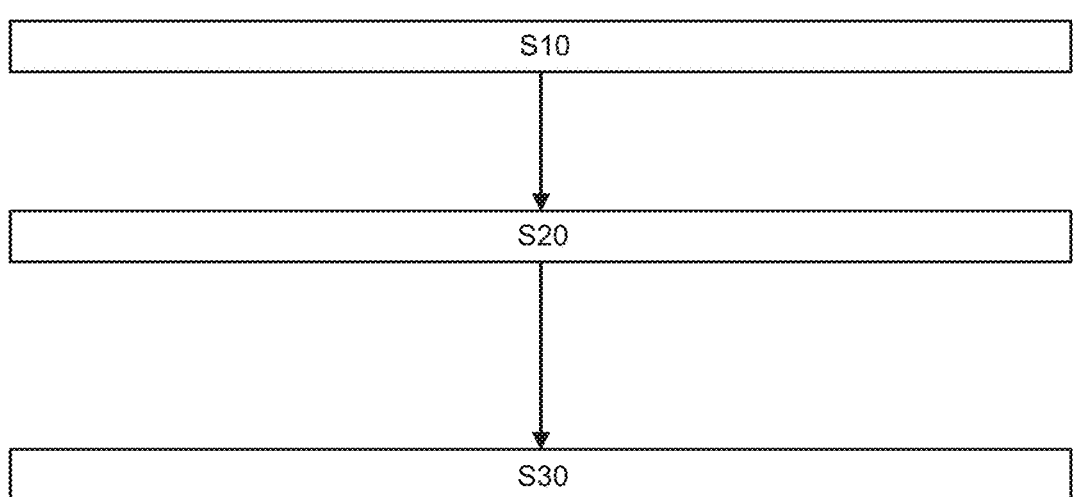

FIG. 2 is a flow chart showing steps of a method 50 for scanning of an object or a plurality of objects in a scanning apparatus. In step S10 the object(s) is (are) manually, for example, placed into a jacket or a plurality of jackets. Of course, any containing vessel may be used. A volume of the jacket surrounding the object may be solid (a solid volume) or may be filled with a filling material such as a powder.

Figure 3:
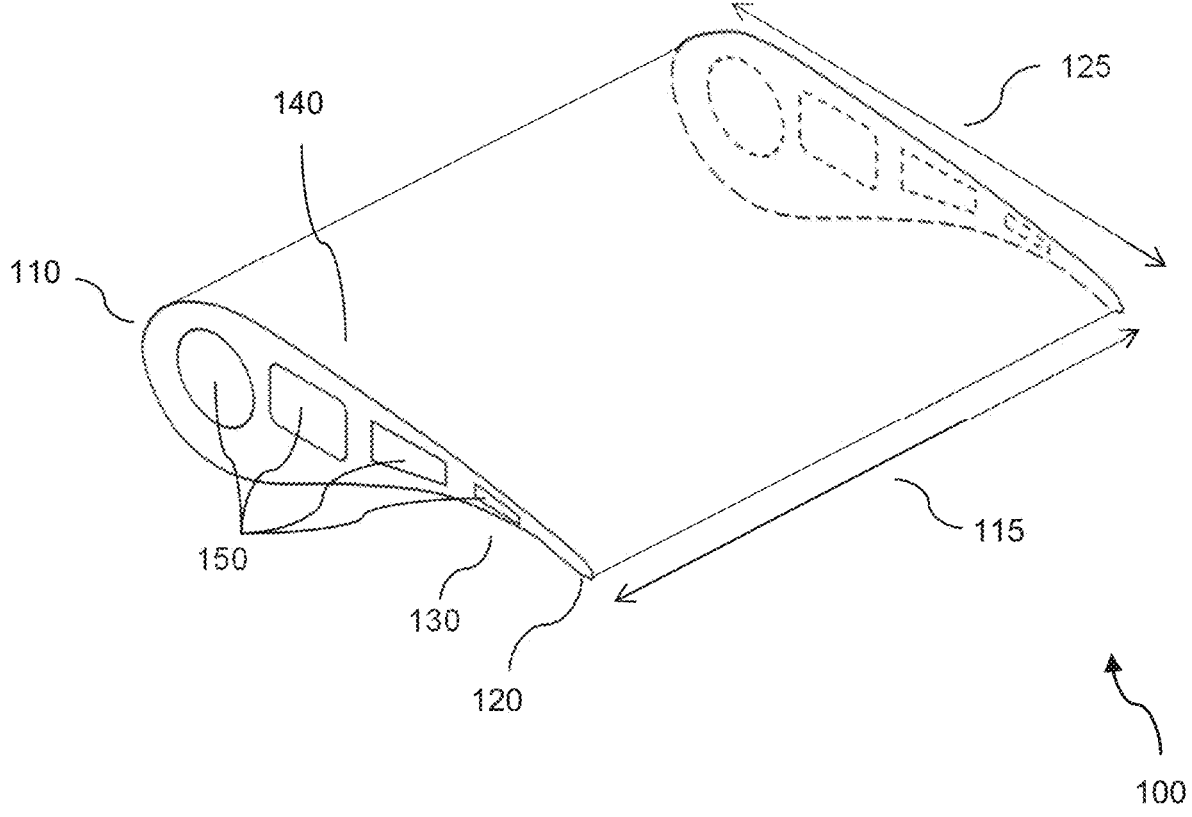
FIG. 3 is a diagonal view of an aerofoil section of a turbine blade.

The filling material or the solid volume may be made from the same material as the object. There may be a border region between the object and the solid volume or filling material. This region may have a different, for example lower, imaging beam attenuation than the object (formed by, for example, a material with a lower density than the object or an air gap or a combination of both). Before placing the object into the jacket, it may be covered with a film or coating or wall or sleeve to protect it from directly contacting the filling material or solid volume. The object placed in the jacket may be a turbine blade 100, for example that which are depicted in FIG. 3. It will be appreciated that the object could, however, take any form. Further, objects with substantially similar or identical construction, such as the turbine blades, may be placed in the jacket. However, of course, different shape objects made from different materials may be placed in the same jacket.

In step S20 the jacket is disposed on a support of a scanning apparatus. The jacket may be held in a jig and so indirectly positioned on the support. The scanning apparatus may be, for example, substantially similar in construction to the 3DCT scanning apparatus 10. The jackets may be disposed in a pattern around the axis of rotation with no part of them intersecting the axis. The objects placed in the jackets may be orientated to form a pattern with rotational symmetry around the axis of rotation.

In S30 the scanning apparatus is operated at multiple relative angles of rotation to produce an image of the object(s) contained within the jacket(s). A projection or projections may be taken at each angle around a complete 360 degrees and a complete volumetric representation of the object(s) contained within the jackets may be obtained from a set of equally angularly spaced projections. The volumetric representation may comprise a plurality of voxels, with each voxel representing a sub-volume of the image. Subsequently the image can be viewed in cross sections, as in known arrangements.

FIG. 3 shows a diagonal view of an aerofoil section of a turbine blade 100. Other parts of the blade, such as a mounting section are less relevant and not shown. The turbine blade in this arrangement is formed from a metal material which may be cast metal, but the teaching herein can be applied to objects of any scannable material.

The turbine blade comprises a leading edge 110, a trailing edge 120, and blade surfaces between these edges, such as a concave surface 130 and a convex surface 140. The concave surface extends in an inwardly curved shape between the leading edge and the trailing edge. The convex surface of the turbine blade extends in a similar manner to the concave surface, but with an outward curve and is opposite to the concave surface. There may be void regions 150 (without the material). For clarity only, exemplary voids are illustrated in FIG. 3. There are four voids illustrated, although it will be apparent to the skilled reader that more or fewer voids may be present.

Sometimes only a small region of a large object is scanned. For example, the aerofoil section (rather than any essentially orthogonal mounting section) is generally of primary interest when CT scanning turbine blades, and in particular the internal structure of the aerofoil section is to be investigated. The aerofoil section may, for example, be considered as the part of interest of the object. A turbine blade within a jacket may be disposed on the support so that the mounting section of the blade intersects the axis of rotation, but the aerofoil section does not. That is, the part of the object to be scanned does not intercept the axis of rotation. As a further example, an object in the shape of the letter 'L' may be disposed in the jacket. It may be that only the vertical part being scanned is offset from the axis but the bottom horizontal part may still intercept the axis of rotation.

As will be appreciated by those of skill in the art, the turbine blade comprises an elongate aerofoil section (part) of the turbine blade having a span 115. Further, a chord 125 maybe be drawn between the extremities of the leading edge and the trailing edge.

Figure 4:
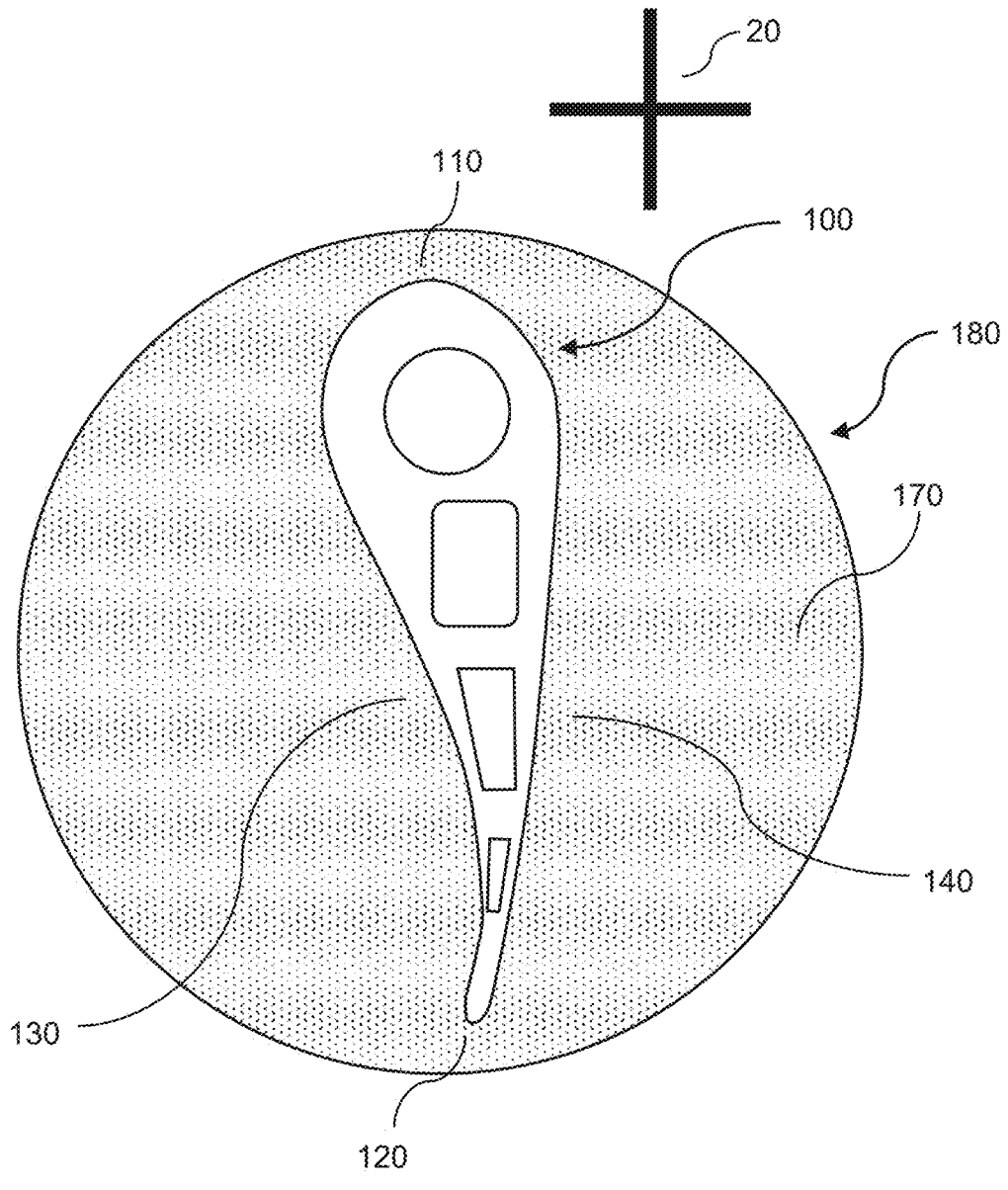
FIG. 4 is a sectional plan view of a turbine blade positioned within a jacket and disposed relative to an axis of rotation of a support in a CT scanning apparatus.

FIG. 4 is a sectional view of the turbine blade disposed within a jacket 180. The jacket, which in FIG. 4 has a circular cross section, but may take any suitable form, contains a filling material 170, for example a powder (or in another arrangements the jacket is formed of a solid volume). For example, the filing material is a powder made from the same material as the object disposed within the jacket. In an arrangement where the object is a turbine blade made from a cast metal, the powder may, for example, be made from the cast metal (or the solid jacket volume may be made from the cast metal, for example). Here, the material of the powder is matched with the material of the object so that the powder and object have the same imaging beam attenuation. That is, as the powder and object are made from the same material, they have the same attenuation coefficient. Hence, it will be appreciated that any material may be used for the powder in this example so long as it has a similar, or substantially similar, imaging beam attenuation as the object disposed within the jacket. Indeed, the same applies if a solid jacket volume is used instead of a filling material.

It will be understood that if more than one object is within the jacket, the objects disposed within the jacket may be made of different materials. The imaging beam attenuation of the filling material or solid jacket volume may be matched to one of the objects, that is the filling material or solid jacket volume may be the same as the material of one of the objects, for example. Alternatively, the composition of the filling material or solid jacket volume may be chosen so that its imaging beam attenuation is an average of the imaging beam attenuations of the objects. The imaging beam attenuation, and the (mass) attenuation coefficient, of the filling material or solid jacket volume may lie within the range of the imaging beam attenuations of the objects.

The jacket may be made from a polymer material; however, it is understood that any material, for example with a relatively low x-ray attenuation coefficient may be suitable.

The blade is disposed within the jacket with the filling material and may be covered by a polymer film (not shown) to prevent contact between the object and the filling material (or in another arrangement a solid volume). Additionally or alternatively, the object may be wrapped or placed within a 'sleeve-like' wall or cooperating walls (preferably contiguous with the object surfaces) to separate it from the filling material or solid volume. It will be appreciated that a plurality of blades and/or, indeed, any object or plurality of objects may be disposed within the jacket. The film may prevent contamination of the object from the filling material. Further, the film may provide a region between the filling material or solid jacket volume and object with an imaging beam attenuation different from the object's imaging beam attenuation. For example, the polymer film may have a lower imaging beam attenuation (or lower density) than the object. Thus, there will be a contrast at the region-object boundary of the scan. This may aid in the identification of the object in the image scan.

The jacket may be disposed on the support of the scanning apparatus centrally, or so that no part of it intercepts the axis of rotation, as shown. As will be appreciated, when the filled jacket is disposed on the support, the support may rotate about the axis of rotation such that the jacket and its contents move, around the axis of rotation, within the x-ray beam cone, in the manner described above with reference to FIG. 1.

Averaging out the material thickness of an object (or plurality of objects) by placing it (them) in a jacket with a filling material, may reduce artifacts caused by the concave wall effect. Regions of the object(s) where x-rays may have been concentrated and scattered may be covered by the filling material, thus reducing scattering and beam hardening effects. The jacket may provide the "ideal" circular cross-section for scanning in which thickness of material to be penetrated is constant for all the projections. The jacket may be, for example, a cylindrical shape or spherical shape depending on the relative motion of the scanning elements in the scanning apparatus. This 'ideal' shape may further improve the image quality and contrast of the scan. Further, the 3DCT scanning parameters may be optimised, hence improving scanning efficiency.

As shown in FIG. 4, the turbine blade within the jacket may be disposed on the support so that the leading edge of the blade is proximal to the axis of rotation and the trailing edge is distal to the axis. In this arrangement, the blade is oriented within the jacket so that the convex surface of the object is closer to the axis than the concave surface but does not face the axis head-on, and the concave surface has no direct "line of sight" to the axis of rotation.

A longitudinal axis of the object can be defined, using the turbine blade in FIG. 3, as being parallel to the span of the turbine blade and extending along the span of the aerofoil section. In FIG. 4 the longitudinal axis is substantially parallel to the axis of rotation (extending into the plane of the page). The object may, however, be orientated to form an angle between the longitudinal axis of the object and the axis of rotation. That is, the object may be placed at an angle within the jacket. Additionally, or alternatively, a longitudinal axis may be defined in a similar way for the jacket and the jacket may be disposed at an angle to the axis of rotation.

Disposing the jacket on the support with the leading edge of the blade closer to the axis of rotation than the trailing edge can be helpful in countering the concave wall effect as the trailing edge is in a "brighter area" of the x-ray scan, away from a central "dark spot" on the axis. In general, an object may have a geometry with a thin region that normally has a darker or lower contrast when scanned. By keeping the object in an orientation where such a geometric element is in the brighter outer half of the scan, the difference in contrast between inner and outer or thicker and thinner regions may be reduced. For turbine blades with a hollow trailing edge, positioning the blade with the trailing edge away from the axis of rotation may keep it in the brighter outer region. The blade may also be orientated to keep the concave and convex surfaces equidistant from the axis of rotation to provide an even image contrast between the surfaces. It will be appreciated that the optimum orientation will be affected by the curvature of the blade. There are certain scenarios, depending on the feature of interest, where orientating the leading edge inside the jacket closer to the axis of rotation may not be desired.

In FIG. 4 the jacket is shown as being disposed totally offset from the axis of rotation. As will be appreciated, this is an example only and the jacket may be disposed so that its centre of symmetry, in the case of, for example, a cylinder, is centred on the axis of rotation. Alternatively, the jacket may be disposed offset from the axis of rotation but with the axis of rotation still contained within the jacket's walls. The inventors surprisingly found that disposing an object (or the part of the object to be scanned) within a jacket offset from the axis of rotation of the support of a 3DCT scanning apparatus may improve image quality and contrast of the CT scan. Positioning the jacket so that it is offset from the axis of rotation may also reduce the concave wall effect. Further, disposing the jacket so that the longitudinal axis of the jacket (or the object within it) is at an angle to the axis of rotation may improve image quality and contrast of the 3DCT scan.

The turbine blade is used by way of example only; the object is not limited to taking this form. The longitudinal axis of the turbine blade is illustrated as substantially parallel to the axis of rotation by way of example only. A longitudinal axis can be defined in a similar manner for a different object.

Figure 5:
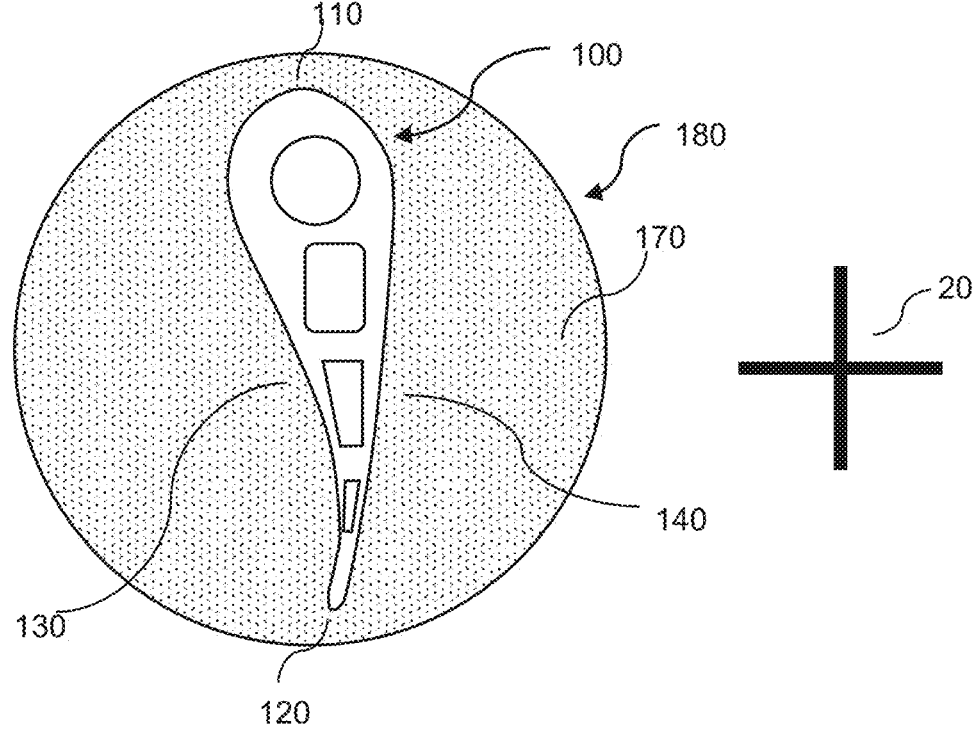
FIG. 5 is another sectional plan view of a turbine blade positioned within a jacket and disposed relative to an axis of rotation of a support in a CT scanning apparatus.

FIG. 5 shows a second arrangement for orientating the object within the jacket relative to the axis of rotation. In this arrangement the jacket is disposed on the support so that the convex surface of the turbine blade is proximal the axis of rotation and the concave surface is distal the axis of rotation, that is the convex surface faces the axis.

The jacket may be disposed on the support so that the axis of rotation is between the leading edge and trailing edge of the blade (or within the extent of the object, in more general terms) when viewed from one side of the CT table, so approximately the centre of the convex surface is facing the axis. This arrangement may improve the image quality of the scan as, by facing the concave surface away from the axis of rotation, artifacts caused by the concave wall effect are reduced.

Figure 6:
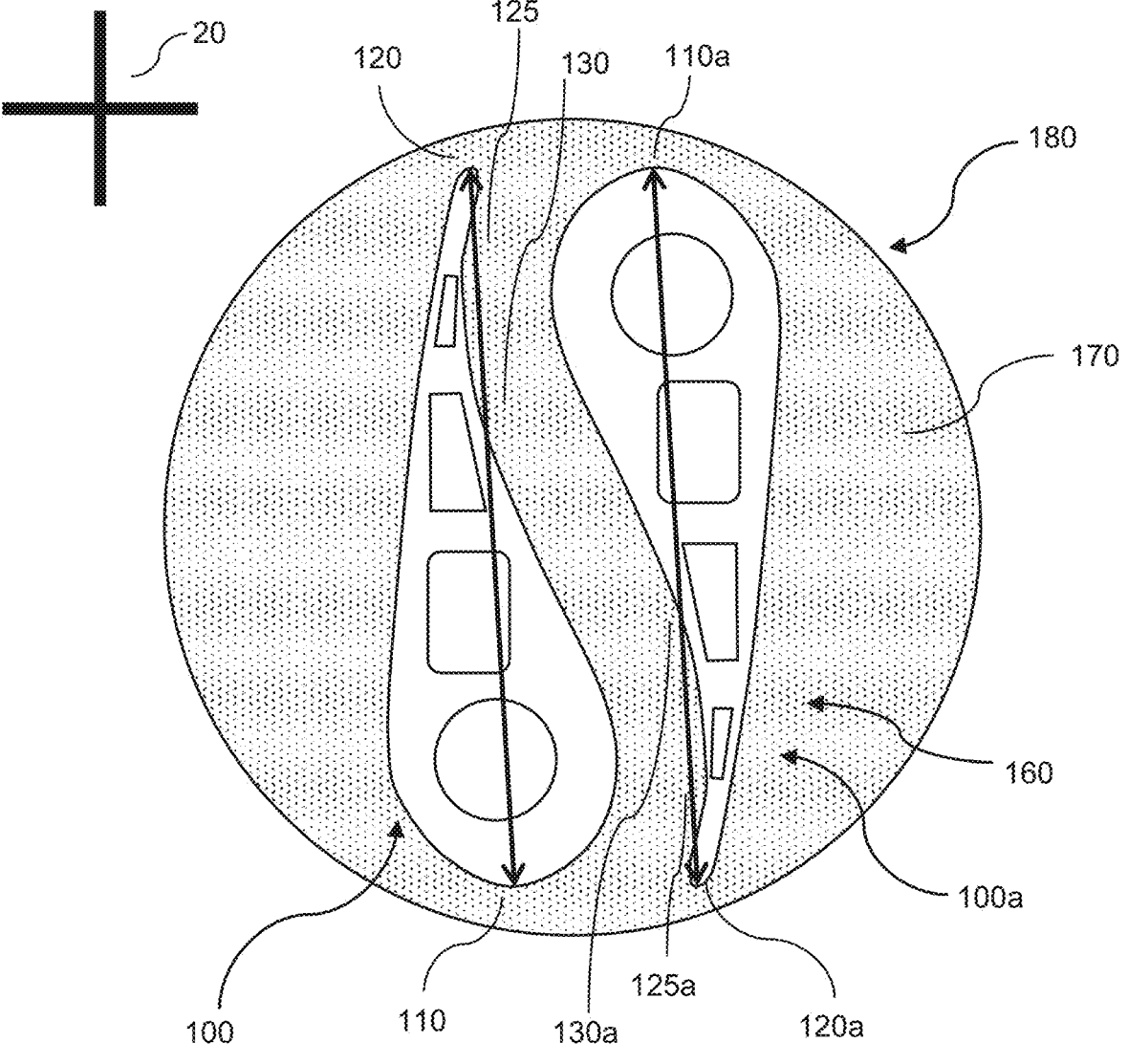
FIG. 6 is a sectional plan view of two turbine blades positioned within a jacket relative to each other and disposed on a support in a CT scanning apparatus.

FIG. 6, a third arrangement, shows a sectional view of the turbine blade previously described disposed adjacent to another turbine blade which has a substantially similar (or identical) construction to the first turbine blade and positioned within the jacket. The turbine blades are disposed within the scanning apparatus in a favourable orientation relative to one another (with a gap occupied by filling material or a solid jacket volume between them). The leading edge of the first blade is adjacent a trailing edge 120a of the second blade and the trailing edge of the first blade is adjacent a leading edge 110a of the second blade, so that they are in a "yin-yang" or "head to toe" configuration. The combined thickness of material to be penetrated by a scanner when the blade surfaces face the x-ray emitting element is evened out in a direction between the leading and trailing edges. Along with the filling material or solid jacket volume providing a constant material thickness for each projection, this configuration may further improve the scan quality. In this arrangement the concave surface of the first blade faces the concave surface 130a of the second blade.

Additionally, and/or alternatively, the orientation of the first object relative to the second object within the jacket may be understood by drawing the chords 125-125a between the extremities of the leading edge and the trailing edge. The orientation of the first blade relative to the second blade is such that the chord 125 of the first blade is substantially parallel to the chord 125*a* and spaced from it in a direction at right angles to the chords.

Disposing a first object relative to a second object in this manner may be considered as making up a base configuration 160. A plurality of base configurations within a plurality of jackets may be oriented relative to one another and the axis of rotation, see for example FIGS. 13 and 14.

As will be appreciated, when the jacket is disposed on the support with the first object and the second object positioned in this configuration, the support rotates about the axis of rotation and the jacket and its contents will rotate together, in their relative orientation as a whole around the axis of rotation within the x-ray beam cone, in the manner described above with reference to FIG. 1. The axis may, for example, extend centrally between the objects, so that they are equally offset from it, or it may extend in any other position, but preferably not through either of the objects. A complete volumetric representation of the two objects within the jacket may be obtained by acquiring a set of CT slices. That is, the first object and the second object are CT scanned simultaneously to produce sectional slices of both objects at the same time. 3DCT scanning efficiency of objects may be improved as a plurality of objects may be scanned simultaneously. For example, such scans may be efficient but still of sufficient quality to issues like miss-formed features in the internal passage.

Figure 7:
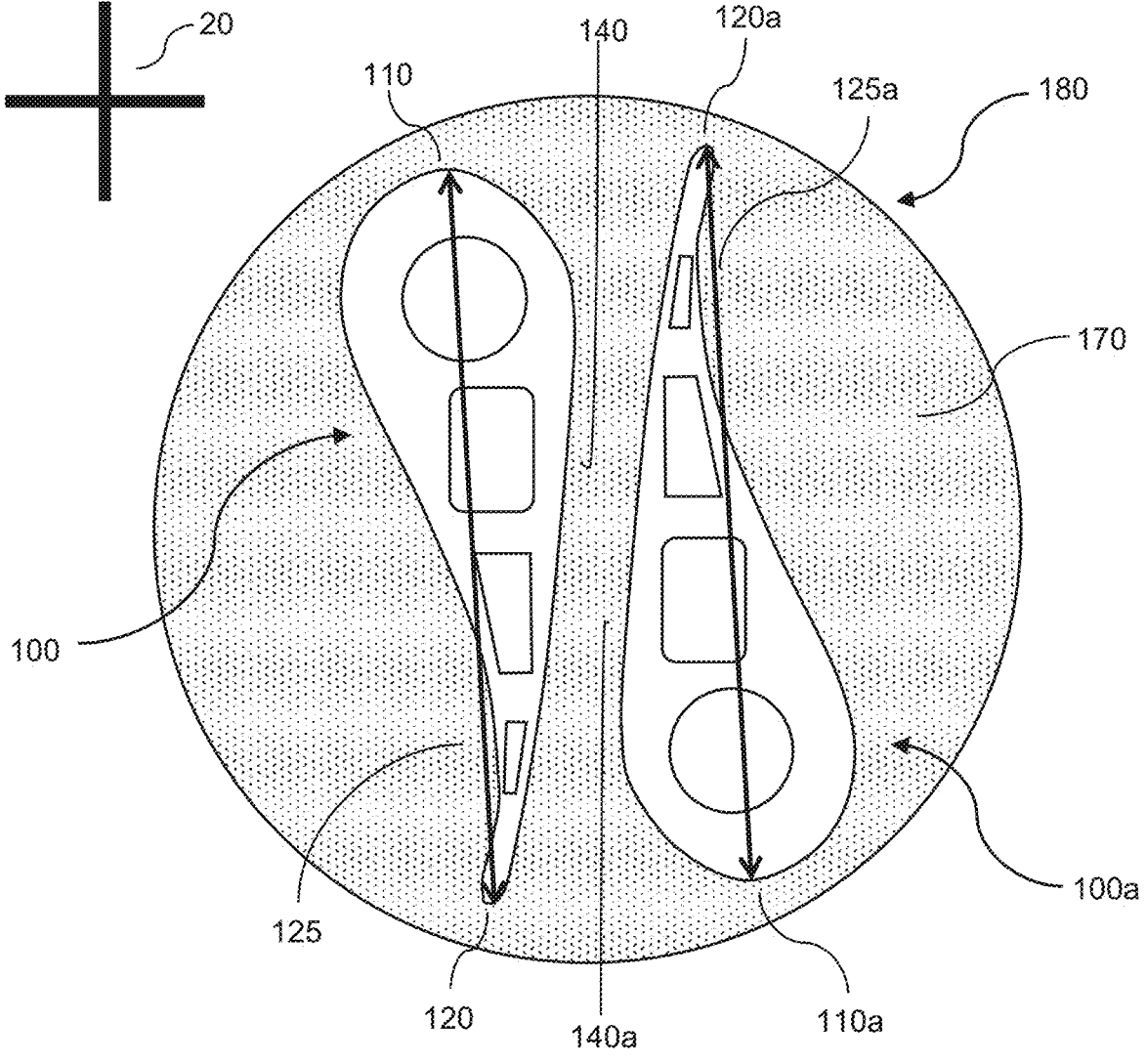
FIG. 7 is another sectional plan view of two turbine blades positioned within a jacket relative to each other and disposed on a support in a CT scanning apparatus.

FIG. 7 shows a fourth arrangement for positioning the first turbine blade and the second turbine blade relative to each other within the jacket. The leading edge of the first blade is adjacent the trailing edge of the second blade and the trailing edge of the first blade is adjacent the leading edge of the second blade, so that the combined thickness is evened out, as mentioned above. The positioning with respect to the axis is the same as in FIG. 6 and the chords are parallel as before. However, in this case, the convex surface 140 of the first blade faces a convex surface 140*a* of the second blade.

A problem the inventors identified when scanning individual turbine blades with an aerofoil cross-section was poor contrast and image quality in either the thinner trailing edge or the thicker leading edge, because different scanning parameters are suitable for the different thicknesses in these two different blade areas. Also, the concave surface and convex blade surfaces can lead to scanning issues. Thus, optimising the 3DCT scan parameters for turbine blade's aerofoil forms (and indeed other objects with uneven thickness across their length) is a problem in the known arrangements and may lead to scan artifacts such as beam hardening and the concave wall effect.

The inventor has come to the realisation that by evening out the material thickness, by placing an object or plurality of objects within a jacket with a filling material or solid jacket volume, the image quality and contrast of the 3DCT scan may be improved as, for example, artifacts from the 3DCT may be reduced or eliminated. By placing the objects in a "head to toe" configuration the material thickness may be further evened out, therefore improving the image quality. The 3DCT scanning efficiency of objects may also be improved as a plurality of objects may be scanned simultaneously.

Figure 8:
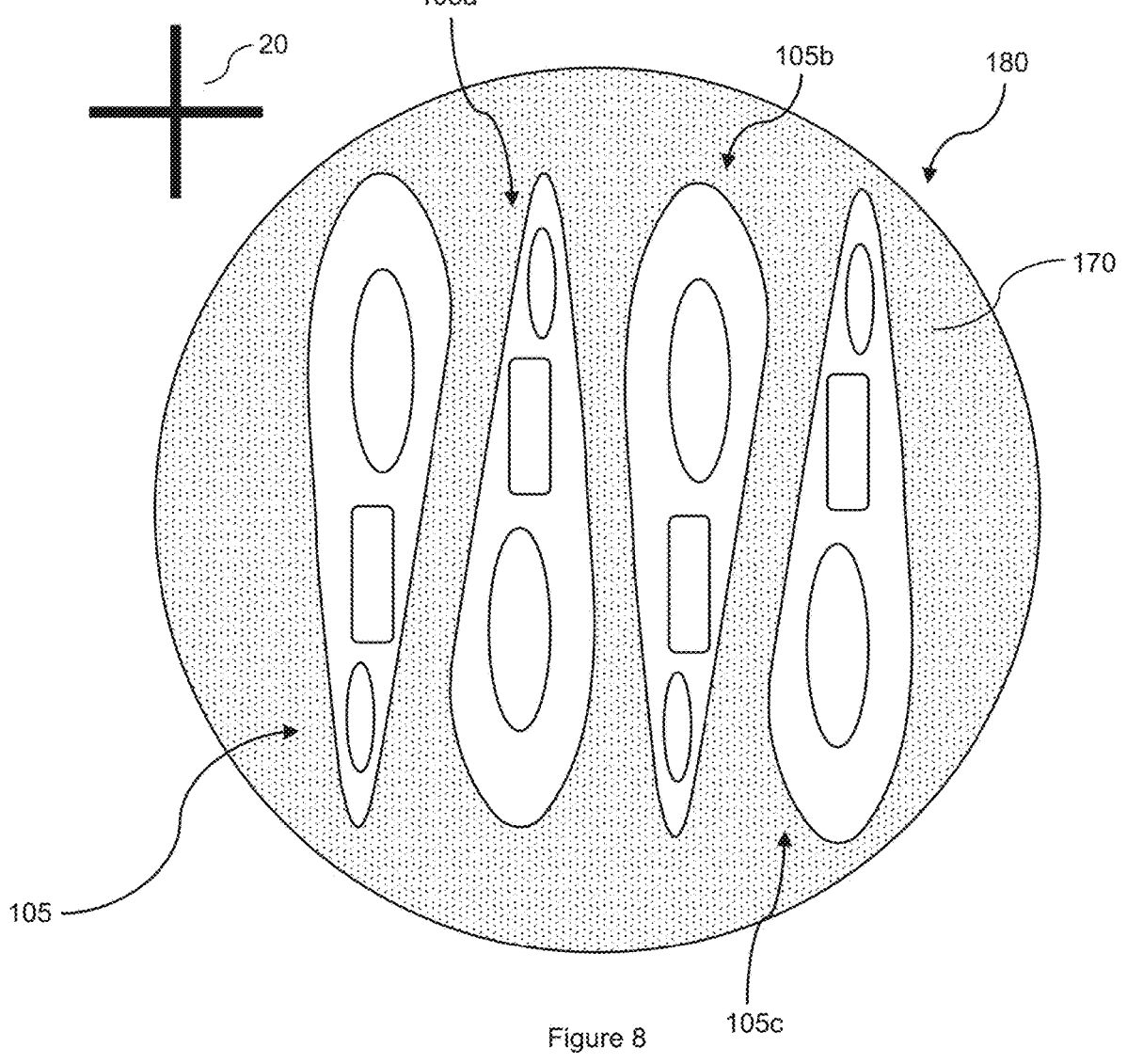
FIG. 8 is a sectional plan view of four turbine blades positioned within a jacket relative to each other and disposed on a support in a CT scanning apparatus.

FIG. 8, a fifth arrangement, shows a sectional plan view of a configuration of four turbine blades 105-105*c* with similar constructions to the turbine blade 100 placed within the jacket. That is, the turbine blades have leading and trailing edges and opposite blade surfaces extending between them. These surfaces may have substantially flat parts, as depicted. The four blades may, however, have substantially similar (or identical) constructions to the blade previously described. In the FIG. 8 configuration, the four blades are in alternating head to toe positioning. Convex and concave blade surfaces may be positioned as per the base configurations of the third arrangement in FIG. 6 or fourth arrangement of FIG. 7. For example, the configuration in FIG. 8 may be realised by disposing two base configurations of two turbine blades aligned and adjacent each other each according to the third arrangement. Alternatively, all the convex surfaces may face the same way, or alternate convex surfaces may face the same way.

Further, it is understood that this arrangement of a line of blades is not limited to four objects and more or fewer may be used.

The four blades may be disposed within the jacket so that the combined thickness of material to be penetrated by the scanner when the blade surfaces face the x-ray emitting element is evened out in a direction between the leading and trailing edges. The aspect ratio of the four blades together (or a line of two or more blades taken together) is lower than the aspect ratio of a single turbine blade. Indeed, this configuration may reduce the combined aspect ratio of a plurality of any objects with relatively high aspect ratios. Placing the blades within the jacket with a filling material or solid jacket volume with an imaging beam attenuation similar, or identical, to one or more of the blades (or with an imaging attenuation in the range of the imaging attenuations of blades) provides a constant material thickness for the projections taken at the relative angles of rotation. The advantages of this are enumerated above.

Additionally, disposing the blades relative to each other in this arrangement, for example, provides a constant material thickness of the blades and therefore may further improve the image quality.

A complete volumetric representation of the four blades may be obtained by acquiring a set of CT slices. That is, the four blades are CT scanned simultaneously to produce sectional slices of all four blades at the same time. 3DCT scanning efficiency of objects may be improved as a plurality of objects may be scanned simultaneously.

Figure 9:
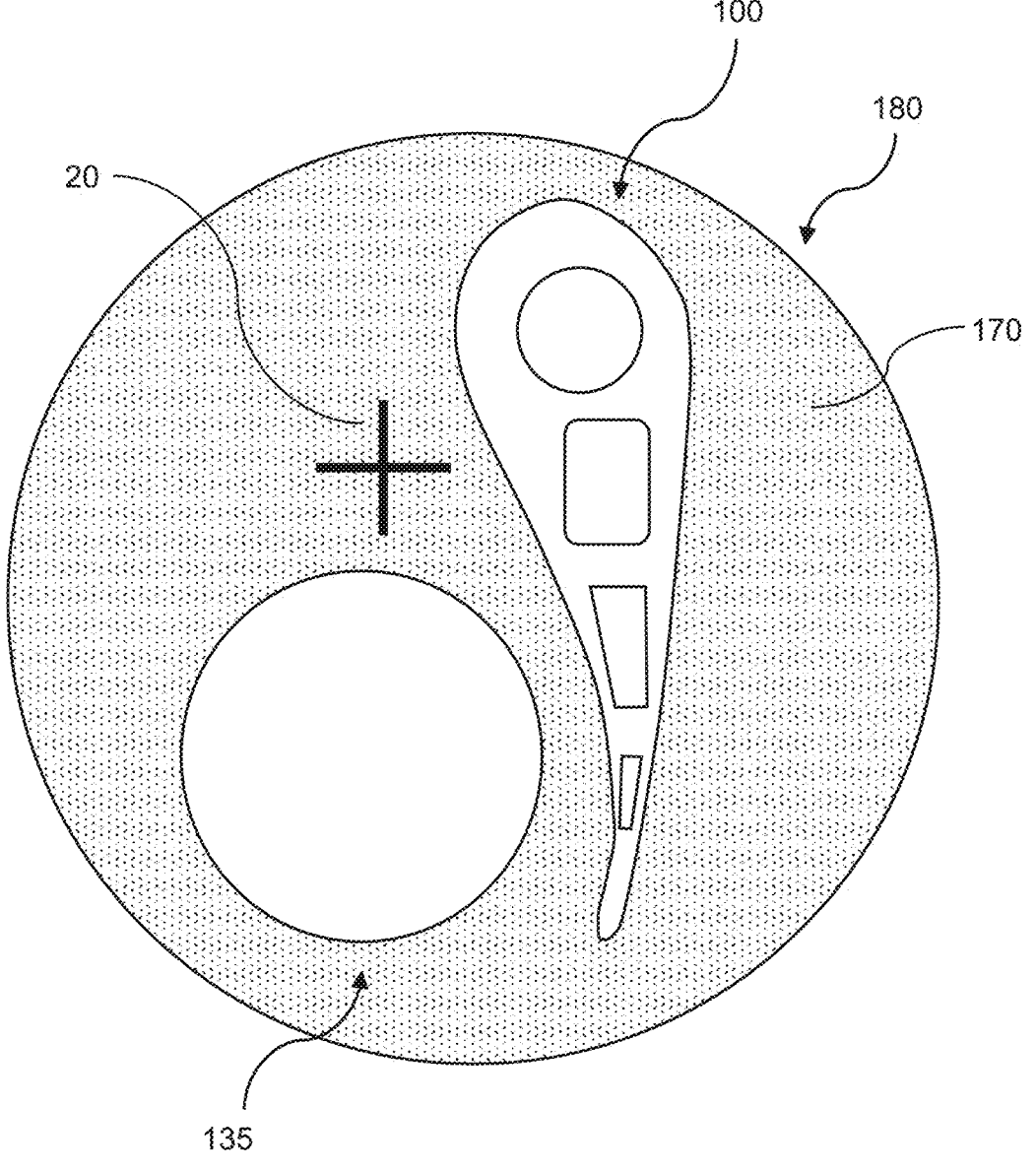
FIG. 9 is a sectional plan view of a turbine blade and a cylindrical object positioned within a jacket relative to each other and disposed relative to an axis of rotation of a support in a CT scanning apparatus.

FIG. 9 shows the turbine blade and an elongate cylinder 135 within the jacket disposed relative to the axis of rotation. The cylinder may be positioned so that it is adjacent the concave surface of the blade. This arrangement may improve the quality of the scan while allowing for a plurality of objects to be scanned at once. As the cylinder effectively fills in the concave wall, artifacts due to, for example, x-rays scattering off the concave surface may be reduced. The cylinder may be made of the same material as the turbine blade. If this is the case, the filling material or solid jacket volume may be chosen so that is has the same imagining beam attenuation as the objects. For example, the filling material or solid jacke3t volume may be made of the same material as the objects. Of course, however, the objects may be made of different materials. The filling material or solid jacket volume may be made of the same material as one of the objects or may be chosen so that its imaging beam attenuation lies in the range of imaging beam attenuations of the objects. That is, for example, the linear attenuation coefficient of the filling material or solid jacket volume may be in between the highest and lowest attenuation coefficients of the objects.

In this arrangement the axis of rotation is shown to be within the walls of the jacket. It will be appreciated that the jacket may be disposed at any location on the support. Hence, the axis of rotation may be at the centre of symmetry of the jacket if, for example, it is cylindrical in shape. Further, the jacket may be offset from the axis of rotation so that no parts to be scanned of the objects or no parts of the objects are intercepted by the axis of rotation, or it may be offset so that no part of the jacket and its contents is intercepted by the axis.

In this example a cylinder and a turbine blade has been used. It is understood that these objects are used by way of example only and that any objects may be placed in the jacket.

Figure 10:
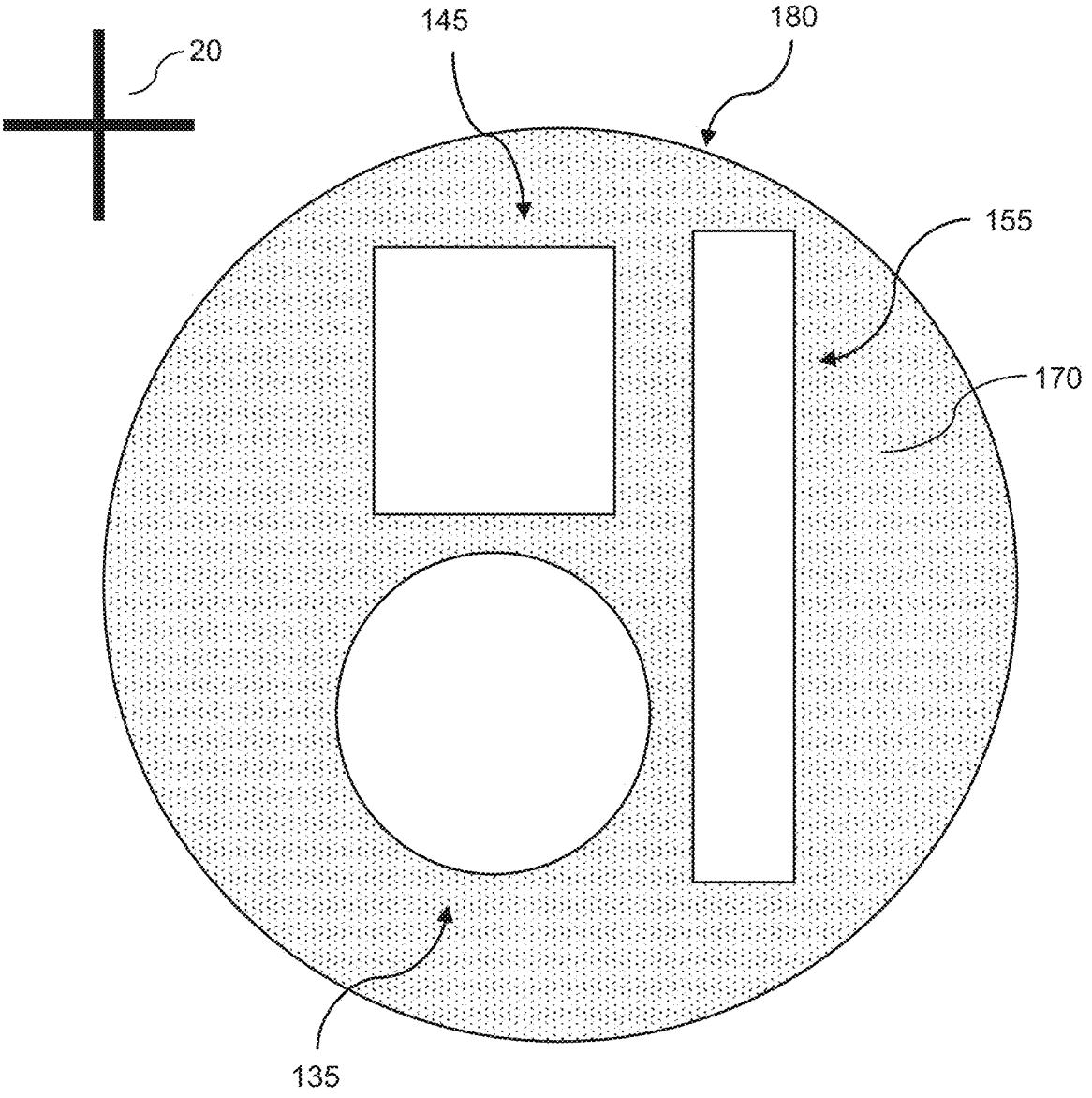
FIG. 10 is a sectional plan view of a cuboid, a cylinder and elongate cuboid, positioned within a jacket and disposed on a support in a CT scanning apparatus.

FIG. 10 shows another arrangement in which different objects are positioned within the jacket. For example, a first object may be the elongate cylinder 135, a second object may be a cuboid 145 and a third object may be an elongate cuboid 155, that has an elongate, high aspect ratio cross section. The combined objects are disposed in a configuration which has a lower aspect ratio than a single one of the objects. For example, the aspect ratio of the combined objects is lower than the aspect ratio of the elongate cuboid.

As for any arrangement in which the objects are made for different materials, the filling material or solid jacket volume may be chosen to be similar, or identical, in its imaging beam attenuation properties as one (or more) of the objects. That is, the filling material or solid jacket volume may be made from the same material as one or more of the objects. Alternatively, the imaging beam attenuation of the filling material or solid jacket volume may be chosen so that it is in the range of the maximum imaging beam attenuation and minimum attenuation of the objects. For example, the attenuation strength of the filling material or solid jacket volume may be an average of the attenuation strengths of the objects within the jacket.

The configuration of the plurality of objects may even out the combined material thickness of the objects. Positioning the objects within the jacket with the filling material or solid jacket volume provides a constant material thickness for each projection at the relative angles of rotation. Positioning the objects in this configuration with the combined material thickness evened out may further improve the image quality of the scan. Additionally, as the aspect ratio of the combined part is lower than the aspect ratio of a single part, 3DCT scanning parameters may be optimised, hence improving scanning efficiency.

It will be appreciated that this arrangement is not limited to simple geometric shapes. Of course, any complex objects, for example turbine blades of any other manufactured parts, may be configured in this manner to provide a constant, or nearly constant, thickness of material for all projections.

Figure 11:
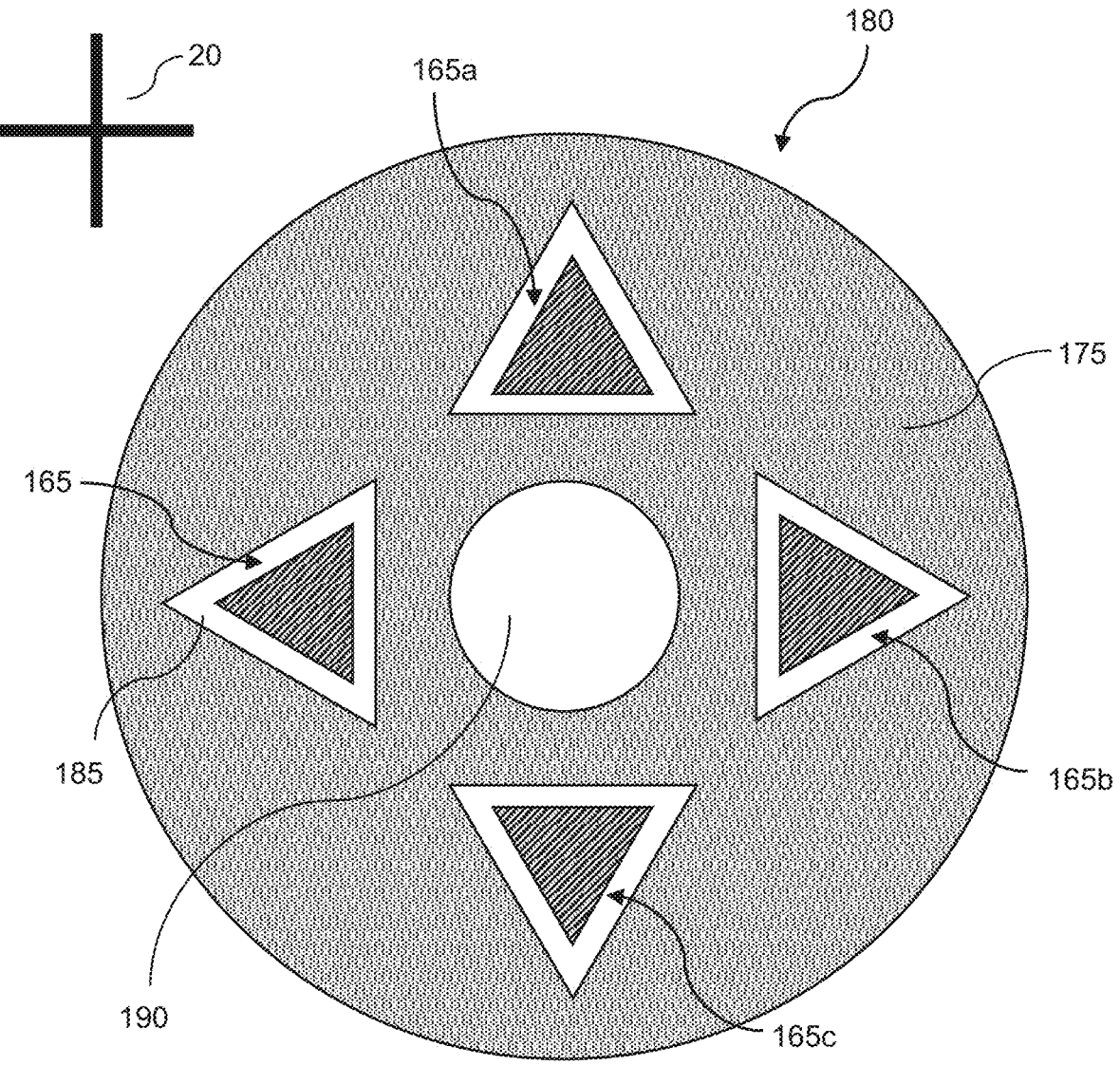
FIG. 11 is a sectional plan view of a plurality of objects positioned within a solid jacket and disposed on a support in a CT scanning apparatus.

FIG. 11 shows an arrangement in which the volume surrounding the object is solid, a solid jacket volume 175, and may form part of the jacket. In this example, there may be cavities 185 in the solid material in which the objects, shows as an example with triangular cross-sections 165-165c, may be placed. The cavities may be in the shape of the object or may have a geometry which is complementary to the geometry of the object. That is, for example, if an object has a concave surface the cavity may have a complementary convex surface so that when the object is placed in the cavity the two surfaces are directly adjacent each other/contiguous. The cavity may, however, take any shape. Additionally, the jacket may have further cavities 190 where objects are not placed. Hence, the jacket may be substantially solid in its construction but, of course may contain numerous cavities. These may be used, for example, to mount the jacket to the support.

The object may be placed in the cavity so that there is a border region between the object and the jacket material with an imaging beam attenuation different from the imaging beam attenuation of the object. For example, this may be from an air gap, or by wrapping the object in a polymer film or wall, as before or both. The difference in density between the region and object may provide a high contrast in the produced image, therefore making identification of the object easier. The region may have a lower density or imaging beam attenuation than the object to aid identification.

The jacket in FIG. 11 is shown as one solid piece; however, it will be appreciated that the jacket may be formed in segments and combined around the object. For example, for a turbine blade with an aerofoil cross section attached to mounting sections at either side, the jacket may be formed in segments which surround only the aerofoil section of the blade. The jacket may be, for example, 3D printed to form a suitable interior geometry to fit around the object. Of course, 3D printing may also be used for a jacket which may be filled with a filling material. Further, it will be appreciated that this arrangement of a jacket with solid jacket volume may be used with any other arrangement herein, for instance as shown in FIGS. 4 to 10. Also, for example, a plurality of jackets with solid jacket volumes may be arranged in a pattern around the axis of rotation, see for example FIG. 12, described hereinafter, or solid volume jackets may be used with any of the arrangements shown in FIGS. 13 to 15.

Figure 12:
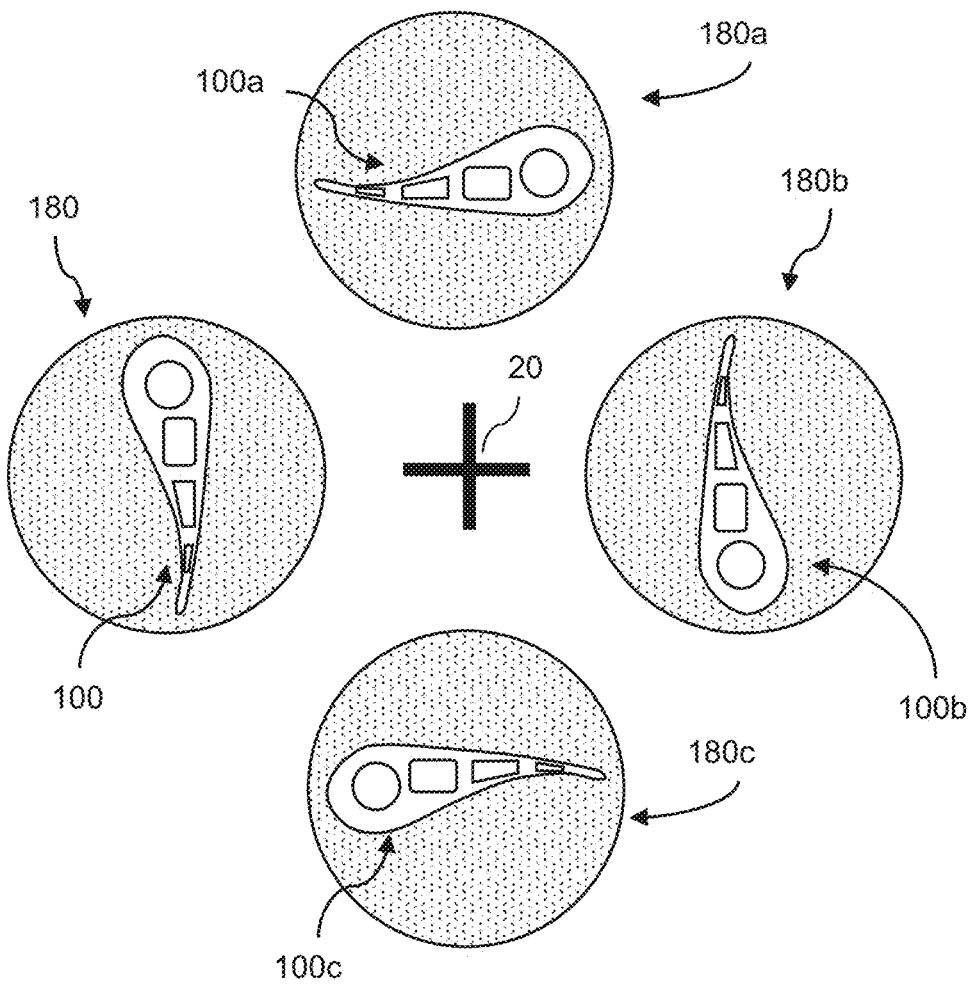
FIG. 12 is a sectional plan view of four turbine blades, each placed within a jacket and disposed relative to an axis of rotation of a support in a CT scanning apparatus.

FIG. 12 shows four turbine blades 100-100c placed within four jackets 180-180c, and the axis of rotation 20. The jackets are disposed on the support so that the four objects are orientated favourably relative to each other and the axis of rotation. Further, the jackets may be positioned relative to each other so that a notional line drawn from the emitting element to the receiving element through the axis of rotation intersects two or more of the jackets for at least a third of the projections.

Considering a notional regular geometric figure (extending parallel to the plane of the support) with four vertices (not shown) and with a centre of symmetry aligned with the axis of rotation, the four jackets are shown positioned on each of the four vertices. The jackets may be positioned so that the single blade in each jacket has a convex surface facing the axis of rotation. However, the reader will understand that the four objects are not limited to this orientation relative to the axis of rotation and may be disposed with their concave surfaces facing the axis of rotation.

The objects (in the jackets) may be oriented to provide rotational symmetry of the pattern of objects about the axis of rotation. In the case where the objects within the jackets are substantially similar, or identical, the order of rotational symmetry may be equal to the number of vertices of the regular geometric figure, as shown in FIG. 12.

It will be appreciated that this arrangement is not limited to four jackets and and/or four objects and/or geometric figures with four vertices. More or fewer than 4 objects may be positioned around the axis of rotation on the vertices of a geometric figure.

Positioning a plurality of jackets on the vertices of a geometric figure may improve the scanning efficiency of the scanning apparatus. As the jackets provide a constant material thickness for each projection taken at the relative angles of rotation, the scanning parameters of the CT scanner may be optimised. In a scan of objects, or parts of objects, offset from the axis of rotation, the inner sides of the objects or parts of the objects will be darker than the outer sides. Introducing more material for the x-rays to penetrate may also improve the scan quality as the power of the scanner may be adjusted to levels where previously image contrast would be reduced. The adjusted power may result in a relatively even contrast across the objects. Of course, other scanning parameters may be adjusted and optimised to improve the quality and/or efficiency of scanning the plurality of objects. Further, the scanning efficiency is improved as a plurality of objects may be scanned at once.

The skilled reader will understand that the orientation of the four objects, within the jackets, relative to each other and the axis of rotation may be varied to improve the image quality and contrast of the objects.

Figure 13:
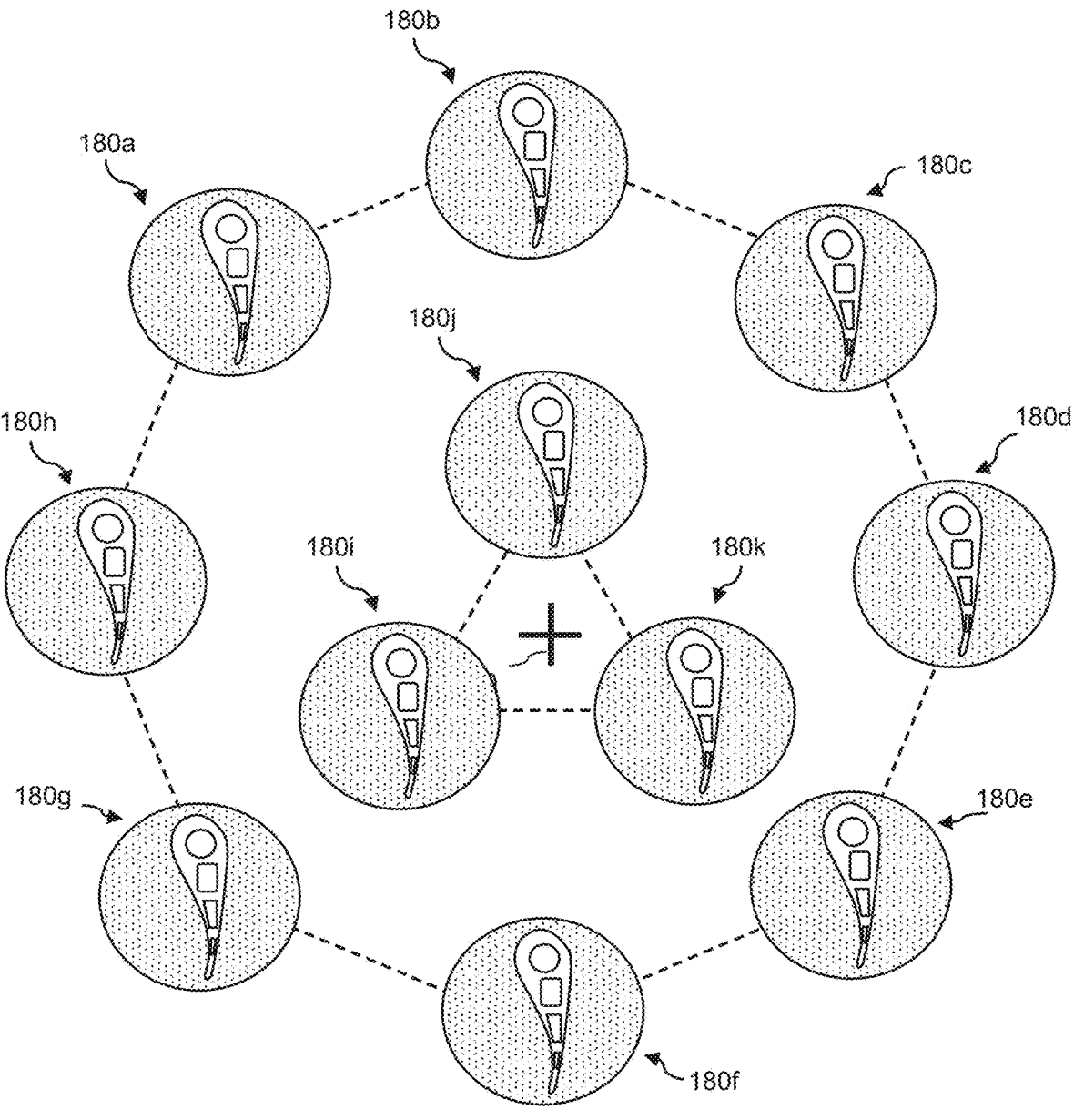
FIG. 13 shows a plurality of turbine blades, each turbine blade from the plurality placed within a jacket and disposed relative to an axis of rotation of a support in a CT scanning apparatus.

FIG. 13 shows a plurality of turbine blades disposed within jackets 180-180*k* with a turbine blade in each jacket. The jackets are disposed on the support relative to the axis of rotation. Considering the notional regular geometric figure, the jackets may be disposed on the vertices of an octagon (shown with a dashed line in the figure) and on the vertices of a further notional regular geometric figure, in this example a triangle (shown with a dashed line in the figure), inside the notional regular geometric figure. Of course, geometric figures with a different number of vertices may be used.

In a scan using jackets with a circular cross-section, for example with longitudinal (vertical) axes parallel to the axis of rotation but offset from the axis of rotation, the inner side of the jackets (closer to axis of rotation) will be darker than the outer side. Introducing more material inside the notional geometric figure by, for example, arranging further jackets in a pattern around an inner notional figure, may improve the scan quality of the jackets (and objects in them) in the outer region. The extra material in the inner region of the support allows for the power of the scanner to be adjusted so that the jackets on the outer geometric figure have a relatively even contrast across their cross-sections.

As will be appreciated, this arrangement may apply to any object placed within the jacket, and objects of different size and shape may be used in the same scan. Additionally or alternatively, an attenuating object or objects not shown here (for example a solid cylinder) may be disposed in the inner region, such as centred on the axis.

Figure 14:
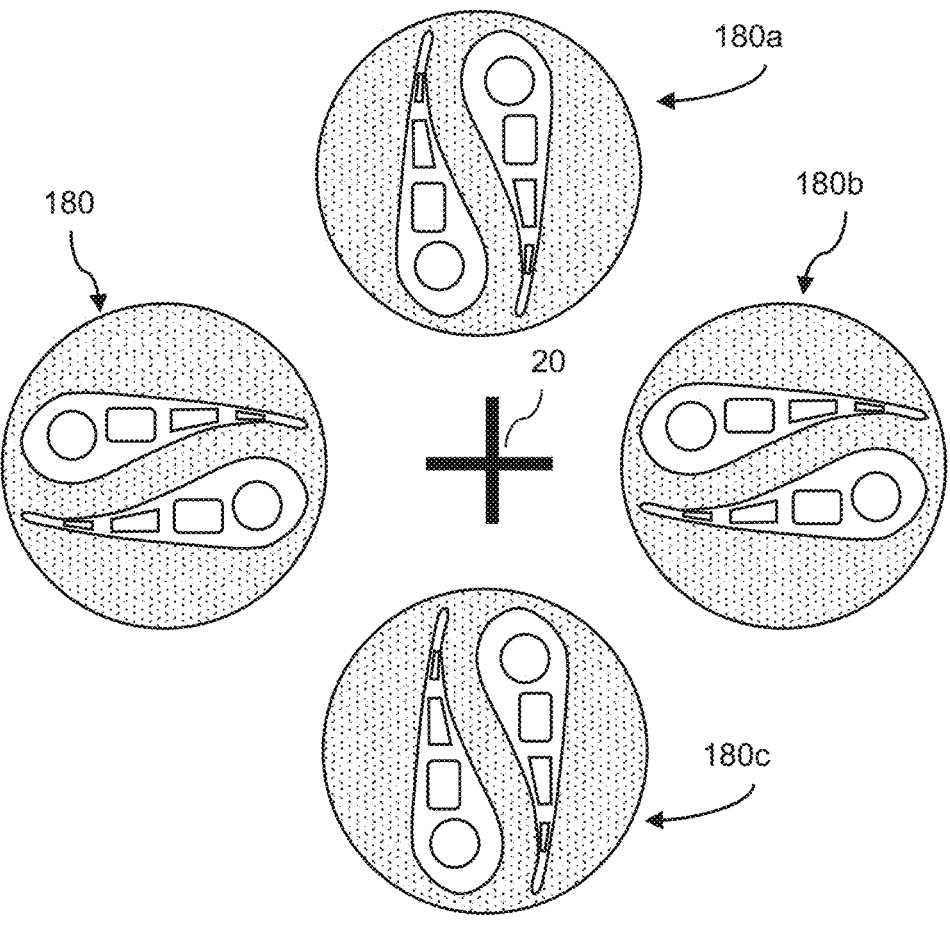
FIG. 14 shows a plurality of combinations of a set/configuration of two turbine blades, as depicted in FIG. 6, each set positioned within a jacket and disposed relative to an axis of rotation of a support in a CT scanning apparatus.

FIG. 14 shows a sectional view of 8 turbine blades, placed within jackets, and the axis of rotation. This arrangement may be realised by considering a notional geometric figure with four vertices and positioned with its centre of symmetry on the axis of rotation. A plurality, in this case four, jackets are placed on the vertices of the geometric figure. The turbine blades may be placed in the jackets relative to one another in an arrangement that resembles any of the first to fifth arrangements disclosed herein, for example.

As will be appreciated, this arrangement is not limited to four sets of the base configuration. More or fewer sets of the base configuration may be used. It is also understood that the number of vertices of the geometric shape is not limited to four, more of fewer vertices may be used. The plurality of base configurations may be disposed on one or more the vertices of the geometric shape and is not limited to being disposed on all vertices.

Figure 15:
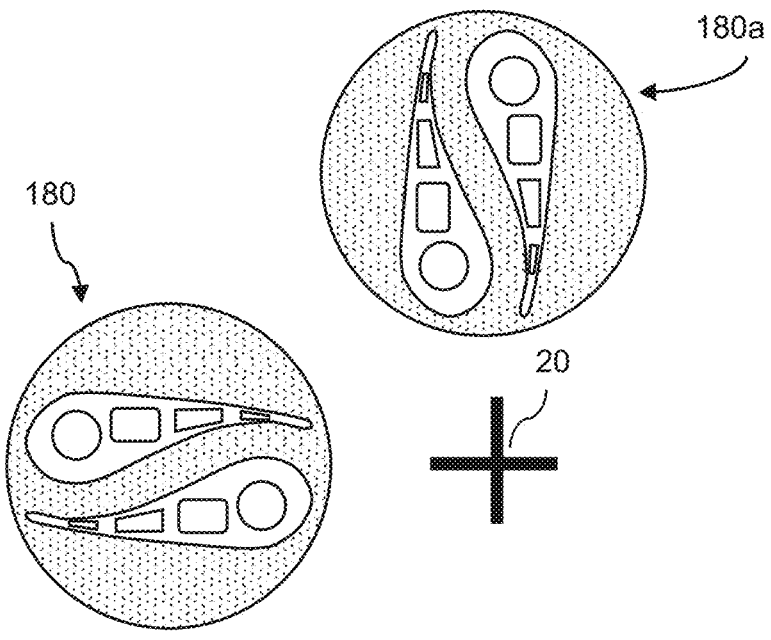
FIG. 15 shows another plurality of combinations of a set/configuration of two turbine blades, as depicted in FIG. 6, each set positioned within a jacket and disposed relative to an axis of rotation of a support in a CT scanning apparatus.

FIG. 15 shows an arrangement similar to that given in FIG. 14 but with only half the vertices of the geometric figure occupied. Considering the notional regular geometric shape (not shown) such as a rectangle or square or triangle for example, with a centre of symmetry aligned with the axis of rotation, a first jacket and a second jacket may be positioned on two adjacent vertices of the geometric figure. In an example where each jacket has a single blade placed within it, the jackets may be disposed on the support so that the trailing edge of the blade in the first jacket is adjacent the leading edge of the blade in the second jacket.

Positioning the first and second jackets on the vertices of the geometric figure may improve the image quality and contrast of the object in the first jacket and/or the object in the second jacket. The skilled reader will understand that the orientation of the first jacket relative to the second jacket may be varied to improve the image quality and contrast of the first blade and/or the second blade.

In the arrangement shown in FIG. 15, the jackets effectively leave half the field clear by only taking up half of the available vertex positions. This asymmetrical arrangement, with half of the available space left empty, provides a better image quality. The blades are shown in a head-to-toe arrangement; however, it will be understood that any arrangement may be used and the arrangements within each jacket may not be the same.

It will be appreciated that the arrangements disclosed herein may improve the image quality and contrast of an object scanned by a CT scanning, or other scanning apparatus. The efficiency of the CT scanning method may be improved as a plurality of objects may be scanned at once. Further, the CT scanning parameters may be optimised for a single object, therefore decreasing scan time and improving scanning efficiency.

It will be understood that the invention is not limited to the arrangements above described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. A method for scanning of an object in a scanning apparatus, the method comprising:
   placing the object into a jacket which surrounds the object or a part of the object to be scanned;
   wherein a volume of the jacket surrounding the object is a metal solid or filled with a metal filling material;
   disposing the jacket on a support of the scanning apparatus, so that the jacket is positioned between an imaging beam emitting element and an imaging beam receiving element oppositely disposed to either side of the support, wherein the support is rotatable relative to the emitting and receiving elements about an axis of rotation to allow creation of an image from projections each taken at a different relative angle of rotation; and the method further comprising:
   operating the scanning apparatus at the multiple relative angles of rotation to produce an image of the object.

2. A method according to claim 1, which further comprises filling the volume surrounding the object within the jacket with the filling material.

3. A method according to claim 1, wherein the filling material or the solid jacket volume has an imaging beam attenuation within 10% of the imaging beam attenuation of the material of the object.

4. A method according to claim 1, wherein the filling material is in the form of powder.

5. A method according to claim 1, wherein the jacket has a circular cross-section; or a cylindrical side wall extending from a base.

6. A method according to claim 1, further comprising a border region surrounding or partially surrounding the object in the jacket with an imaging beam attenuation different from the imaging beam attenuation of the object.

7. A method according to claim 6, wherein the border region is formed by inserting the object into a protective film or wall or sleeve.

8. A method according to claim 1, wherein the jacket is positioned on the support offset from the axis of rotation.

9. A method according to claim 1, wherein the object is a turbine blade with a leading edge and a trailing edge separated by blade surfaces.

10. A method according to claim 1, for scanning a plurality of objects, wherein a plurality of objects is placed within the jacket, and/or a plurality of jackets is disposed on the support.

11. A method according to claim 10, wherein a plurality of jackets is disposed on the support so that a notional line drawn from the emitting element to the receiving element through the axis of rotation intersects two or more of the plurality of jackets for at least a third.

12. A method according to claim 10, wherein the objects are turbine blades each with a leading edge and a trailing edge separated by a concave blade surface opposite to a convex blade surface.

13. A method according to claim 10, wherein the jackets are positioned in a pattern on vertices of a notional regular geometric figure centred on the axis of rotation, optionally wherein further jackets or objects are positioned in a pattern on inner vertices of a further notional regular geometric figure centred on the axis of rotation and inside the notional regular geometric figure.

14. A method according to claim 13, wherein the objects are oriented within the jackets to provide rotational symmetry of the pattern of objects and jackets about the axis of rotation.

15. A method according to claim 13, wherein the jackets are positioned on some but not all of the vertices of the notional regular geometric figure.

16. A method according to claim 13, wherein there is a plurality of objects in a jacket at a vertex of the notional figure, the objects being grouped in a configuration within the jacket directly adjacent to each other and centred on the vertex.

17. A method according to claim 16, wherein the objects are elongate and a shape of the configuration formed by the combined shape of the objects in the configuration has a lower aspect ratio than a single one of the objects.

18. A method according to claim 17, wherein the objects are turbine blades, each with a leading edge and a trailing edge separated by blade surfaces, and wherein the blades are positioned in the configuration within the jacket in alternate head to toe configuration with the leading edge of one blade positioned adjacent to the trailing edge of the adjacent blade.

19. A method according to claim 1, wherein the scanning apparatus is a computational tomography, CT, scanning apparatus, and wherein the imaging beam is an x-ray.

20. A combination of a scanning apparatus for scanning of an object and a jacket in the scanning apparatus, the scanning apparatus comprising:

a support for the object; and an imaging beam emitting element and an imaging beam receiving element oppositely disposed to either side of the support, wherein the support is rotatable relative to the emitting and receiving elements about an axis of rotation to allow creation of an image of the object from projections each taken at a different relative angle of rotation; and the filled jacket comprising:

a jacket which surrounds an object or a part of an object to be scanned, wherein a volume of the jacket surrounding the object is a metal solid or filled with a metal filling material, wherein the jacket is positioned on the support; so that when the scanning apparatus is operated at the multiple relative angles of rotation it produces an image of the object within the jacket.

\* \* \* \* \*